(12) United States Patent
Bass

(10) Patent No.: US 7,537,565 B2
(45) Date of Patent: May 26, 2009

(54) SURGICAL RETRACTOR WITH ROTATING BLADES

(76) Inventor: Daniel Bass, 300 San Carlos Ave., El Granada, CA (US) 94018

( * ) Notice: Subject to any disclaimer, the term of this patent is extended or adjusted under 35 U.S.C. 154(b) by 163 days.

(21) Appl. No.: 11/353,128

(22) Filed: Feb. 14, 2006

(65) Prior Publication Data

US 2007/0073111 A1      Mar. 29, 2007

Related U.S. Application Data

(60) Provisional application No. 60/720,485, filed on Sep. 27, 2005.

(51) Int. Cl.
*A61B 1/32* (2006.01)

(52) U.S. Cl. .................. 600/219; 600/228; 600/232; 600/234

(58) Field of Classification Search .............. 600/201, 600/213, 219, 222, 225, 232, 234, 224, 228
See application file for complete search history.

(56) References Cited

U.S. PATENT DOCUMENTS

| | | | | |
|---|---|---|---|---|
| 497,064 A * | 5/1893 | Van Meter | .................. | 600/234 |
| 1,706,500 A * | 3/1929 | Smith | .................. | 600/232 |
| 2,642,862 A * | 6/1953 | Jackson | .................. | 600/232 |
| 4,263,899 A | 4/1981 | Burgin | | |
| 4,852,552 A * | 8/1989 | Chaux | .................. | 600/232 |
| 5,052,373 A * | 10/1991 | Michelson | .................. | 600/217 |
| 5,512,038 A | 4/1996 | O'Neal et al. | | |
| 5,813,978 A | 9/1998 | Jako | | |
| 5,846,193 A * | 12/1998 | Wright | .................. | 600/215 |
| 5,902,233 A | 5/1999 | Farley et al. | | |
| 5,931,777 A | 8/1999 | Sava | | |
| 5,944,658 A * | 8/1999 | Koros et al. | .................. | 600/232 |
| 6,206,828 B1 * | 3/2001 | Wright | .................. | 600/232 |
| 6,572,540 B2 | 6/2003 | Dobrovolny | | |
| 6,663,562 B2 | 12/2003 | Chang | | |
| 7,147,599 B2 * | 12/2006 | Phillips et al. | .................. | 600/232 |
| 2001/0041828 A1 * | 11/2001 | Deckman et al. | .................. | 600/232 |
| 2004/0002629 A1 * | 1/2004 | Branch et al. | .................. | 600/210 |

\* cited by examiner

*Primary Examiner*—Cris L Rodriguez
*Assistant Examiner*—Hao D Mai
(74) *Attorney, Agent, or Firm*—Kramer & Amado PC

(57) ABSTRACT

A surgical retractor includes a retractor body and a retractor arm. The retractor arm includes a first portion and a second portion. The first portion is attached to the retractor body and the second portion is rotatably attached to the first portion. The second portion is configured to retain a retractor blade and to rotate about an axis parallel to a line drawn along a length of the retractor arm.

12 Claims, 4 Drawing Sheets

SURGICAL RETRACTOR WITH ROTATING BLADES

CROSS-REFERENCE TO RELATED APPLICATIONS

This application claims the benefit of U.S. Provisional Patent Application No. 60/720,485, filed Sep. 27, 2005, and entitled, "Surgical Retractor With Rotating Blades."

BACKGROUND

Surgical procedures often require the creation of a surgical exposure to allow a surgeon to reach deeper regions of the body. The surgical exposure is usually started with an incision of a suitable depth. Surgical instruments known as retractors are then inserted into the incision and used to pull back skin, muscle and other soft tissue to permit access to the desired area.

A typical retractor is made up of a retractor body attached to one or more retractor blades. Retractor blades are smooth, thin plates with dull edges that are inserted into the incision to pull back the tissue. Retractor blades come in many different sizes depending on the particular application and physical characteristics of the patient. Retractor blades may be slightly curved or completely flat and may have end prongs of various configurations to make it easier to pull back tissue. The retractor blades can be attached to a wide variety of retractor bodies, such as for hand-held and self-retaining retractors.

Hand-held retractors are made up of a simple grip attached to a retractor blade. The retractor blade may be fixed or interchangeable. The retractor blade is inserted into the incision and then the grip is used to pull back the blade to create the surgical exposure. The grip may be attached at an angle to the retractor blade to make it easier to pull back on the blade. Hand-held retractors must be held in place by hand in order to maintain the surgical exposure.

Self-retaining retractors have specialized retractor bodies that allow them to maintain a surgical exposure without needing to be held in place by hand. Two common self-retaining retractors are longitudinal retractors and transverse retractors.

Longitudinal retractors have a retractor body made up of two seesawing arms with a pair of opposed retractor blades on their respective ends. The retractor body typically has a ratcheting mechanism to lock apart the two opposed retractor blades and hold them in place. This maintains the surgical exposure without the need for the retractor to be held in place by hand. The two arms may be hinged to facilitate access to the retraction site. The retractor blades may be either fixed or interchangeable.

Transverse retractors have a retractor body made up of a transverse rack with a fixed arm and a sliding arm. The fixed arm and sliding arm have opposed retractor blades on their respective ends. The sliding arm typically has a turnkey that operates a ratcheting mechanism, which ratchets the sliding arm away from the fixed arm and locks apart the retractor blades. The two arms may be hinged to facilitate access to the retraction site. The retractor blades may be either fixed or interchangeable.

The retractors in use today retract the opening created in the body of the patient in a uniform manner. If the surgeon needs a large opening near the spine, for instance, the opening in the body of the patient must be retracted in a uniform manner. This creates significant trauma for the patient and increases the patient's recovery time.

What is needed is a surgical retractor that gives a surgeon a suitable area within the body to work on the patient while reducing the required incision size. This reduces trauma to the patient and reduces the patient's recovery time.

SUMMARY

According to an embodiment, a surgical retractor includes a retractor body and a retractor arm. The retractor arm includes a first portion and a second portion. The first portion is attached to the retractor body and the second portion is rotatably attached to the first portion. The second portion is configured to retain a retractor blade and to rotate about an axis parallel to a line drawn along a length of the retractor arm.

BRIEF DESCRIPTION OF THE DRAWINGS

Examples of the invention are illustrated, without limitation, in the accompanying figures in which like numeral references refer to like elements and wherein.

DETAILED DESCRIPTION

For simplicity and illustrative purposes, the principles are shown by way of examples of systems and methods described. In the following description, numerous specific details are set forth in order to provide a thorough understanding of the examples. It will be apparent however, to one of ordinary skill in the art, that the examples may be practiced without limitation to these specific details. In other instances, well known methods and structures are not described in detail so as not to unnecessarily obscure understanding of the examples.

In an example, a surgical retractor includes a retractor body and retractor arms. The retractor arm includes a first portion attached to the retractor body and a second portion rotatably attached to the first portion. The second portion also includes a connector for receiving a retractor blade. The second portion may be attached to the first portion by a pivot pin and may rotate trough a range of motion of up to 90 degrees. However, when used in the body of a patient, a range of motion of up to about 45 degrees may be practical. The first portion may includes a thumb screw in engagement with the second portion for forcing the second portion to rotate with respect to the first portion. Additionally, a spring may be located between the first and second portions in order to bias the second portion into a neutral position such that the retractor blades are generally parallel.

Figures 1, 2A, 2B:
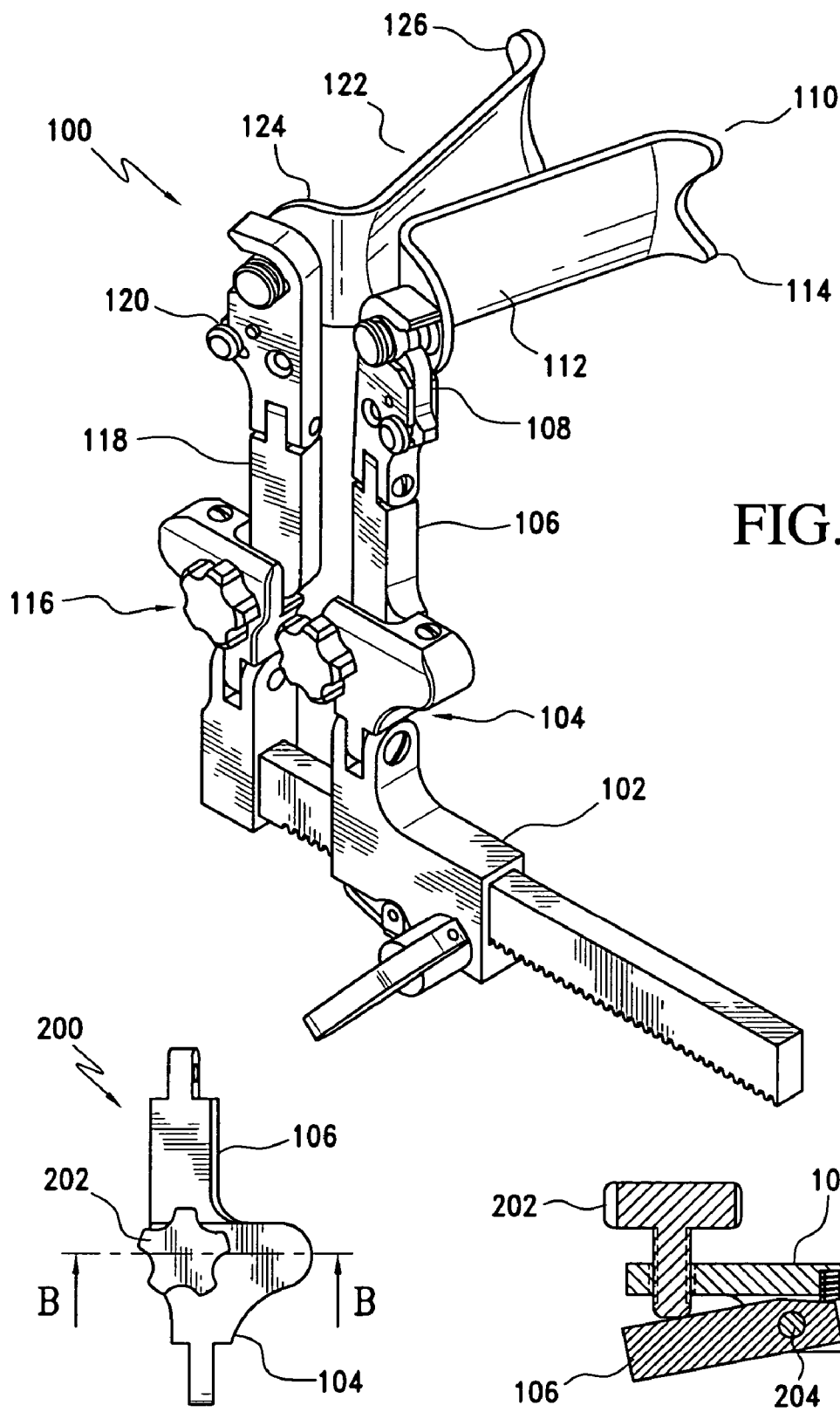
FIG. 1 shows a perspective diagram of a surgical retractor with rotating blades in accordance with an embodiment.
FIGS. 2A and 2B shows perspective and cut away diagrams of a surgical retractor arm in accordance with an embodiment.

With reference first to FIG 1, there is shown a surgical retractor 100 including a retractor body 102. A first retractor arm including a first portion 104 and a second portion 106 is connected to the retractor body 102 by the first portion 104. The second portion 106 is rotatably attached to the first portion 104 and includes at a distal end a connector 108 for receiving a retractor blade 110. The connector 108 may be configured in a variety of manners. One example of a connector for use with a surgical retractor blade is described in U.S. application Ser. No. 11/219,847 by Daniel Bass and entitled "Connector for A Surgical Retractor". This application is hereby incorporated by reference in its entirety.

The retractor blade 110 includes a proximal end 112 near the connector 108 and a distal end 114 which is inserted into the body of a patient. The second portion 106 which retains the retractor blade 110 may rotate around an axis parallel to a line drawn along a length of the retractor arm. This rotation causes the distal end 114 of the retractor blade 110 to tilt or angle thus exposing a larger area inside the body of a patient without significantly increasing an insertion point. Because the distal end 114 of the retractor blade 110 moves through a larger range of motion than the proximal end 112, the insertion point may be smaller than the area inside the body of the patient.

The surgical retractor 100 also includes a second retractor arm including a first portion 116 and a second portion 118 connected to the retractor body 102 by the first portion 116. The second portion 118 is rotatably attached to the first portion 116 and includes at a distal end a connector 120 for receiving a retractor blade 122. The retractor blade 122 includes a proximal end 124 near the connector 120 and a distal end 126 which is inserted into the body of a patient. The second portion 118 which retains the retractor blade 122 may rotate around an axis parallel to a line drawn along a length of the retractor arm. This rotation causes the distal end 126 of the retractor blade 122 to tilt or angle thus exposing a larger area inside the body of a patient without significantly increasing an insertion point. Because the distal end 126 of the retractor blade 122 moves through a larger range of motion than the proximal end 124, the insertion point may be smaller than the area inside the body of the patient.

When the retractor blades 110 and 122 are inserted into the body of a patient, the second portions 106 and 118 of the retractor arms may be rotated. This causes the distal ends 114 and 126 to separate and expose a larger area inside the body of the patient than the area of the insertion point. The proximal ends 112 and 124 of the retractor blades 110 and 122 may lie near the insertion point but may not significantly increase the insertion area as the proximal ends 112 and 124 move through a smaller range of motion than the distal ends 114 and 126 of the retractor blades 110 and 122.

FIG. 2A shows a segment 200 of one of the retractor arms from FIG. 1. The segment 200 includes the first portion 104 and the second portion 106 of the retractor arm. The first portion 104 of the retractor arm includes a thumb screw 202. The thumb screw 202 screws into the first portion 104 and engages the second portion 106. When the thumb screw 202 is tightened, force is exerted upon the second portion 106 causing rotation around an axis parallel to a line drawn along a length of the retractor arm. When the thumb screw 202 is loosened, the force is removed and the second portion 106 may rotate back to the original position.

FIG. 2B shows a cutaway view of the segment 200 along line B shown in FIG. 2A. As shown in FIG. 2B, the second portion 106 is connected to the first portion 104 by a pivot pin 204. A spring 206 biases the second portion 106 into a neutral position. The neutral position is a position wherein the retractor blade 110 is generally perpendicular to the retractor body 102. In other words, the neutral position is the position wherein the retractor blades 110 and 122 are generally parallel to one another. When the thumb screw 202 is tightened, force is exerted upon the second portion 106 overcoming the force of the spring 206 and causing rotation. When the thumb screw 202 is loosened, the force is removed and the spring 206 moves the second portion 106 into the neutral position.

Figure 2C:
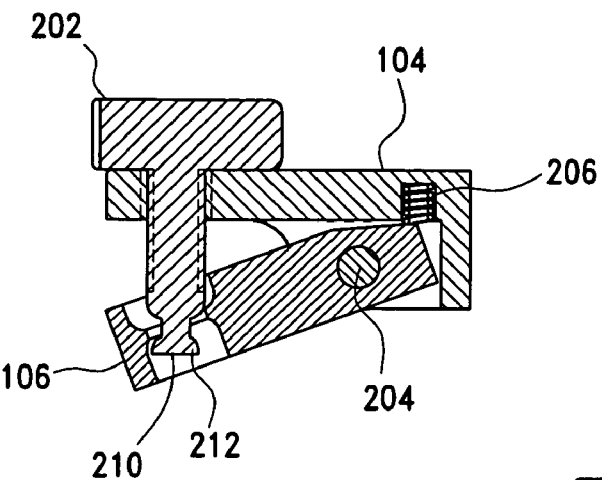
FIG. 2C shows a cut away diagram of a surgical retractor arm in accordance with another embodiment.

FIG. 2C shows a cutaway view, of another example, of the segment 200 along line B shown in FIG. 2A. As shown in FIG. 2C, the second portion 106 is connected to the first portion 104 by a pivot pin 204. A spring 206 biases the second portion 106 into a neutral position. The neutral position is a position wherein the retractor blade 110 is generally perpendicular to the retractor body 102. In other words, the neutral position is the position wherein the retractor blades 110 and 122 are generally parallel to one another. When the thumb screw 202 is tightened, force is exerted upon the second portion 106 overcoming the force of the spring 206 and causing rotation. When the thumb screw 202 is loosened, the force is removed and the spring 206 moves the second portion 106 into the neutral position. The thumb screw 202, in this example, includes a step-down end portion 210 with threads and an associated retaining nut 212. Additionally, the second portion 106 includes an aperture. The step-down end portion 210 of the thumb screw 202 fits through the aperture while the remaining portion does not. The retaining nut 212 is then screwed onto the step-down end portion 210 thus locking the thumb screw 202 to the second portion 106. In this arrangement, the thumb screw 202 is able to apply pressure to the second portion 106 forcing the second portion 106 into rotation to and from the neutral position. This example reduces the work required from the spring 206.

Figure 3:
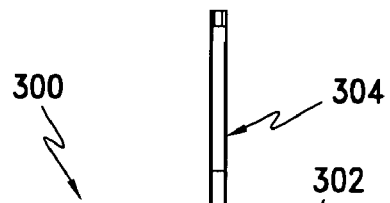
FIG. 3 shows an illustrated view of a dilator in the body of a patient in accordance with an embodiment.
Figure 3:
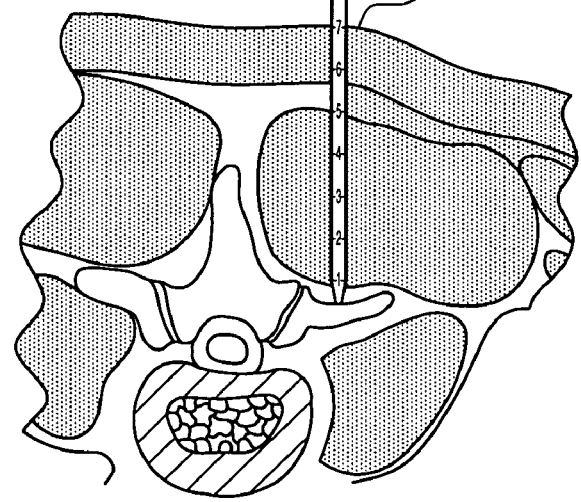
Figure 4:
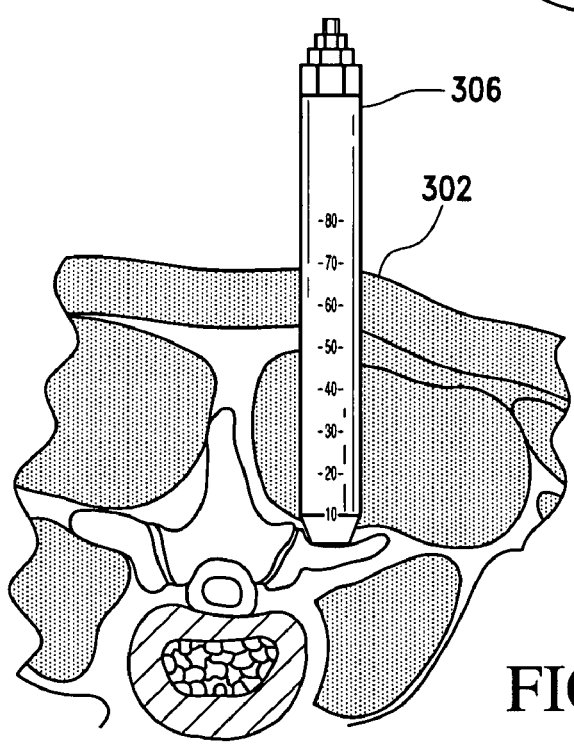
FIG. 4 shows an illustrated view of a further dilated area in the body of a patient in accordance with an embodiment.

FIG. 3 shows the body of a patient 300. First, an opening 302 is made in the body 300. A dilator 304 is then inserted. In FIG. 4, the opening 304 is increase in diameter by inserting an additional dilator 306. Any number of dilators may be inserted to increase the diameter of the opening 302 to a size for receiving the blades 110 and 122 of the retractor 100.

Figure 5:
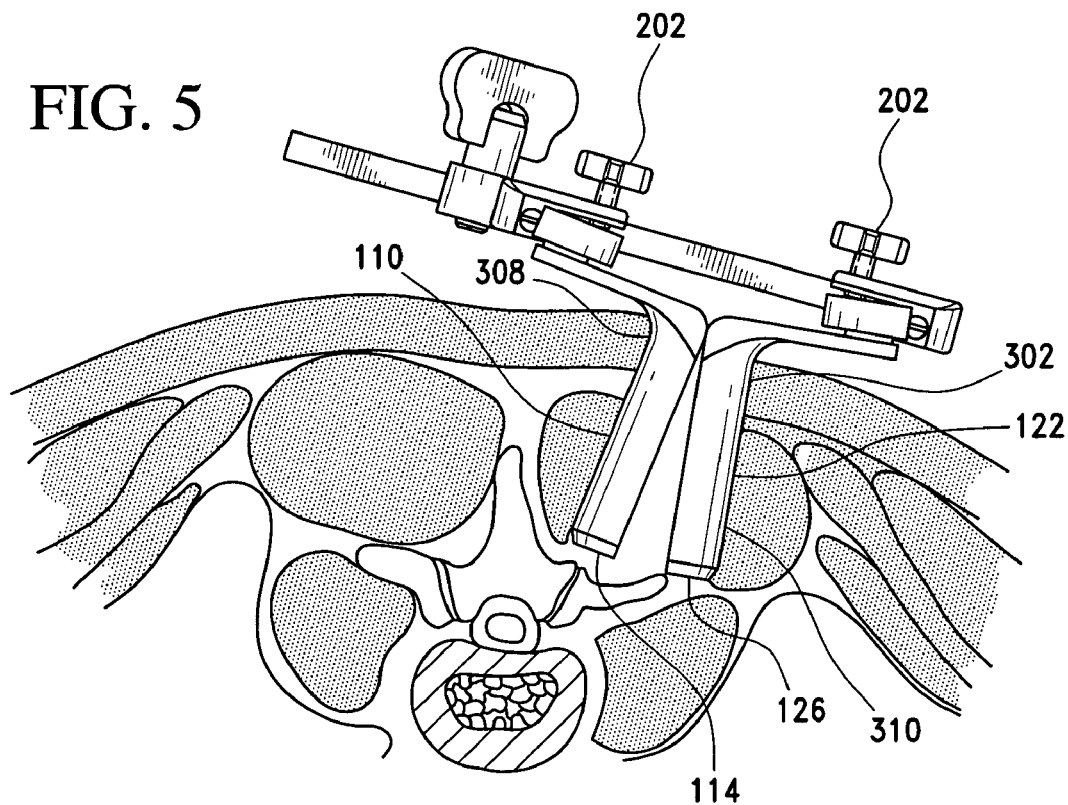
FIG. 5 shows an illustrated view of a surgical retractor with rotating blades used in the body of a patient in accordance with an embodiment.

In FIG. 5, the blades 110 and 122 of the retractor 100 are inserted into the opening 302 of the body. The thumb screws 202 are adjusted to tilt the retractor blades 110 and 122 thus separating the distal ends 114 and 126. Thus a distal end 310 of the opening is larger in area than the proximal end 308 of the opening 302. This allows the surgeon to perform work on the patient while reducing the incision size and the amount of trauma to the patient.

Figure 6:
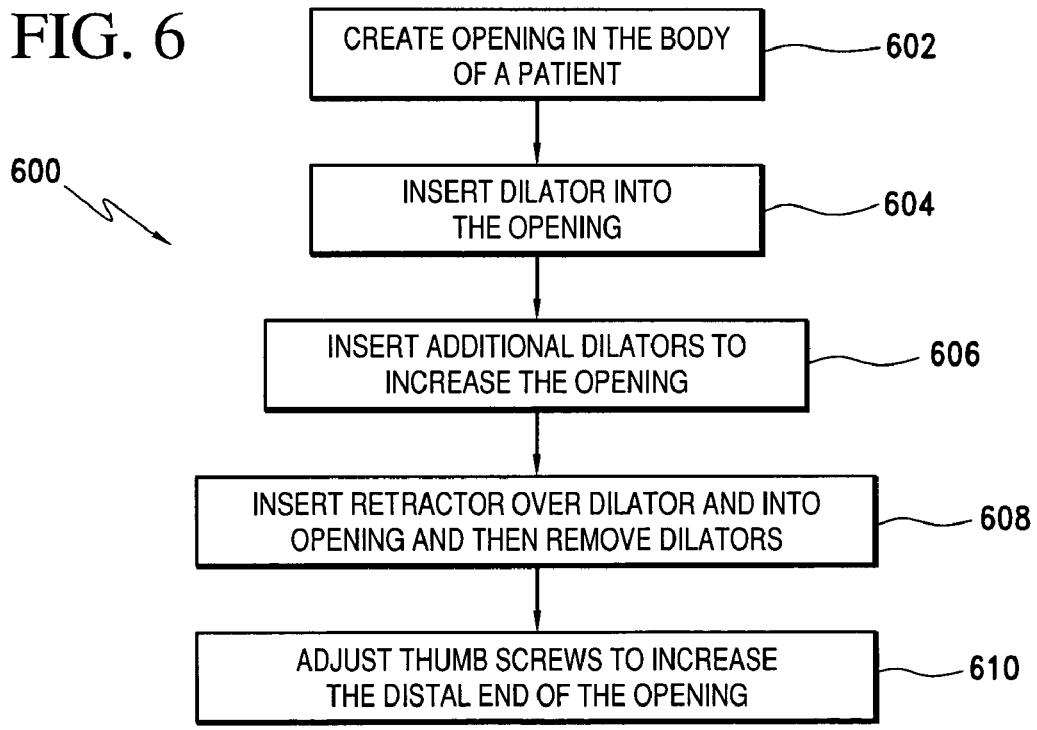
FIG. 6 shows a flow diagram of a method for using a surgical retractor in accordance with an embodiment.

FIG. 6 shows a flow diagram of a method 600 for using the retractor 100. The following description of the method 600 is made with reference to the retractor 100 illustrated in FIG. 1 and patient 300 as shown in FIGS. 3-5, and thus makes reference to the elements cited therein. The following description of the method 600 is one manner in which the retractor 100 may be used. In this respect, it is to be understood that the following description of the method 600 is but one manner of a variety of different manners in which such a retractor may be used.

In the method 600, an incision is made in the body 300 of a patient at step 602. A dilator 304 is then inserted into the incision to create an opening 302 at step 604. Additional dilators 306 may also be inserted into the opening 302 to increase the size at step 606. The blades 110 and 122 of the surgical retractor 100 are inserted over the dilators 306 into the opening 302 and the dilators 304 and 306 are removed at step 608. The thumb screws 202 are then adjusted to increase the area near the distal end 310 of the opening 302 at step 610. In this manner, the distal end 310 of the opening is increased without significantly increase the size of the proximal end 308 of the opening 302 in the body 300.

Figure 7:
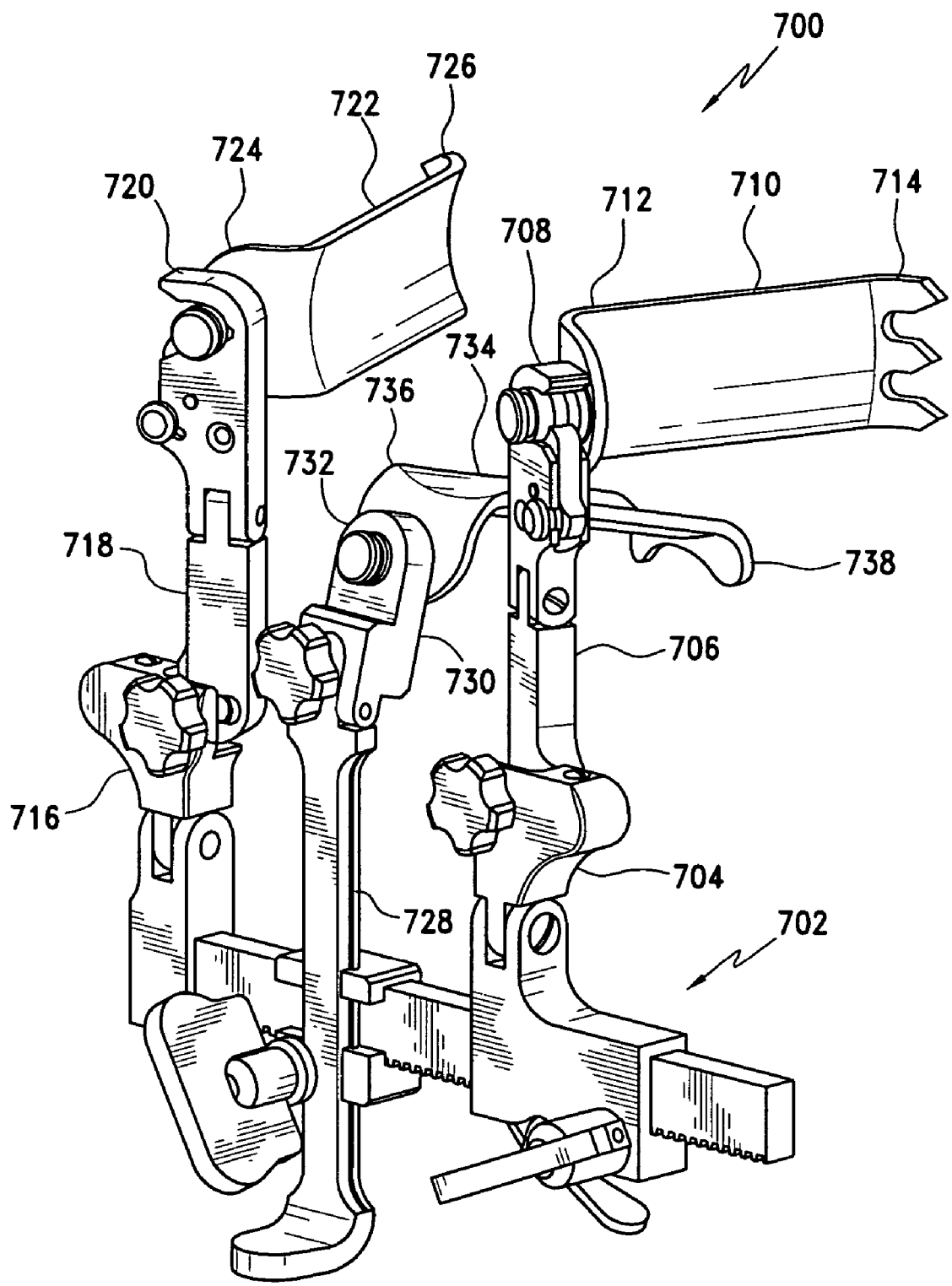
FIG. 7 shows a perspective diagram of a surgical retractor with rotating blades in accordance with another embodiment.

FIG. 7 shows a surgical retractor 700 including a retractor body 702. A first retractor arm including a first portion 704 and a second portion 706 is connected to the retractor body 702 by the first portion 704. The second portion 706 is rotatably attached to the first portion 704 and includes at a distal end a connector 708 for receiving a retractor blade 710. The connector 708 may be configured in a variety of manners as described above in reference to FIG. 1.

The retractor blade 710 includes a proximal end 712 near the connector 708 and a distal end 714 which is inserted into the body of a patient. The second portion 706 which retains the retractor blade 710 may rotate around an axis parallel to a line drawn along a length of the retractor arm. This rotation causes the distal end 714 of the retractor blade 710 to tilt or angle thus exposing a larger area inside the body of a patient without significantly increasing an insertion point. Because the distal end 714 of the retractor blade 710 moves through a larger range of motion than the proximal end 712, the insertion point may be smaller than the area inside the body of the patient.

The surgical retractor 700 also includes a second retractor arm including a first portion 716 and a second portion 718 connected to the retractor body 702 by the first portion 716. The second portion 718 is rotatably attached to the first portion 716 and includes at a distal end a connector 720 for receiving a retractor blade 722. The retractor blade 722 includes a proximal end 724 near the connector 720 and a distal end 726 which is inserted into the body of a patient. The second portion 718 which retains the retractor blade 722 may rotate around an axis parallel to a line drawn along a length of the retractor arm. This rotation causes the distal end 726 of the retractor blade 722 to tilt or angle thus exposing a larger area inside the body of a patient without significantly increasing an insertion point. Because the distal end 726 of the retractor blade 722 moves through a larger range of motion than the proximal end 724, the insertion point may be smaller than the area inside the body of the patient.

The surgical retractor 700 also includes a third retractor arm including a first portion 728 and a second portion 730 connected to the retractor body 702 by the first portion 728. The second portion 730 is rotatably attached to the first portion 728 and includes at a distal end a connector 732 for receiving a retractor blade 734. The retractor blade 734 includes a proximal end 736 near the connector 732 and a distal end 738 which is inserted into the body of a patient. The second portion 730 which retains the retractor blade 734 may rotate around an axis perpendicular to a line drawn along a length of the retractor arm. This rotation causes the distal end 738 of the retractor blade 734 to tilt or angle thus exposing a larger area inside the body of a patient without significantly increasing an insertion point. Because the distal end 738 of the retractor blade 734 moves through a larger range of motion than the proximal end 736, the insertion point may be smaller than the area inside the body of the patient.

When the retractor blades 710, 722, and 734 are inserted into the body of a patient, the second portions 706, 718, and 730 of the retractor arms may be rotated. This causes the distal ends 714, 726, and 738 to separate and expose a larger area inside the body of the patient than the area of the insertion point. The proximal ends 712, 724, and 736 of the retractor blades 710, 722, and 734 may lie near the insertion point but may not significantly increase the insertion area as the proximal ends 712, 724, and 736 move through a smaller range of motion than the distal ends 714, 726, and 738 of the retractor blades 710, 722, and 734.

What has been described and illustrated herein are examples of the systems and methods described herein along with some of their variations. The terms, descriptions and figures used herein are set forth by way of illustration only and are not meant as limitations. Those skilled in the art will recognize that many variations are possible within the spirit and scope of these examples, which are intended to be defined by the following claims and their equivalents in which all terms are meant in their broadest reasonable sense unless otherwise indicated.

What is claimed is:

1. A surgical retractor comprising:
   a retractor body;
   a first retractor arm having a first portion and a second portion, the first portion attached to the retractor body and the second portion rotatably attached to the first portion and configured to retain a first retractor blade, wherein the second portion rotates about an axis parallel to a line drawn along a length of the first retractor arm;
   a second retractor arm having a third portion and a fourth portion, the third portion attached to the retractor body and the fourth portion rotatably attached to the third portion and configured to retain a second retractor blade, wherein the fourth portion rotates about an axis parallel to a line drawn along a length of the second retractor arm;
   a third retractor arm having a fifth portion and a sixth portion, the fifth portion attached to the retractor body and the sixth portion rotatably attached to the fifth portion and configured to retain a third retractor blade, wherein the sixth portion rotates about an axis perpendicular to a line drawn along a length of the third retractor arm; and
   a spring located between the first and second portions, the spring biasing the second portion into a position such that the first retractor blade is substantially normal to a line drawn parallel to the first portion of the first retractor arm.

2. The surgical retractor of claim 1, wherein the second portion may rotate through a range of motion of about 90 degrees.

3. The surgical retractor of claim 2, wherein the second portion may rotate through a range of motion of about 45 degrees.

4. The surgical retractor of claim 1, further comprising:
   a pivot pin for connecting the second portion to the first portion.

5. The surgical retractor of claim 4, further comprising:
   a thumb screw mounted on the first portion of the first retractor arm and in contact with the second portion of the first retractor arm, such that, adjustment of the thumb screw causes rotation of the second portion of the first retractor arm.

6. The surgical retractor of claim 5, wherein the second portion of the first retractor arm includes an aperture and wherein the thumb screw includes an end portion attached to the second portion through the aperture.

7. A surgical retractor comprising:
   a retractor assembly;
   a first retractor arm having a first portion and a second portion, the first portion attached to the retractor assembly;
   a second retractor arm having a third portion and a fourth portion, the third portion attached to the retractor assembly;

a third retractor arm having a fifth portion and a sixth portion, the fifth portion attached to the retractor assembly;

means for rotatably attaching the sixth portion of the third retractor arm to the fifth portion, wherein the second portion and the sixth portion rotate about non-parallel axes;

means for rotatably attaching the second portion of the first retractor arm to the first portion; and means for biasing the second portion of the first retractor arm in a first position.

8. The surgical retractor of claim 7, further comprising:

means for rotating the second portion of the first retractor arm to a second position.

9. The surgical retractor of claim 8, wherein the second portion of the first retractor arm comprises means for retaining a retractor blade, wherein, in the first position, the retractor blade is generally normal to a line parallel with the retractor assembly, and wherein, in the second position, the retractor blade is angled with respect to the line parallel with the retractor assembly.

10. A method of using a surgical retractor comprising:

creating an opening in a body of a patient, the opening having a proximal end near the skin of the patient and a distal end further inside the body of the patient;

providing a surgical retractor including three retractor arms, a first retractor arm having a first portion and a second portion rotatably attached to the first portion, the second portion retaining a first retractor blade, wherein the second portion rotates about an axis parallel to a line drawn along a length of the first retractor arm, a second retractor arm having a third portion and a fourth portion rotatably attached to the third portion, the fourth portion retaining a second retractor blade, wherein the fourth portion rotates about an axis parallel to a line drawn along a length of the second retractor arm, and a third retractor arm having a fifth portion and a sixth portion rotatably attached to the fifth portion, the sixth portion retaining a third retractor blade and rotating about an axis perpendicular to a line drawn along a length of the third retractor arm, wherein each retractor blade has a proximal end and a distal end;

inserting the first, second, and third retractor blades within the opening;

rotating the second portion of the first retractor arm, the fourth portion of the second retractor arm, and the sixth portion of the third retractor arm so that distal ends of the first, second, and third retractor blades enlarge the distal end of the opening without substantially increasing the proximal end of the opening; and biasing at least one of the second portion of the first retractor arm, the fourth portion of the second retractor arm, and the sixth portion of the third retractor arm in a first position.

11. The method of claim 10, further comprising:

adjusting a thumb screw to rotate at least one of the first portion of the first retractor arm, the third portion of the second retractor arm, and the fifth portion of the third retractor arm.

12. The method of claim 10, further comprising:

creating an incision in the body of the patient;

inserting a dilator through the incision for creating the opening; and dilating the opening to a size for receiving the first, second, and third retractor blades.

* * * * *